(12) United States Patent
Spiridigliozzi et al.

(10) Patent No.: US 7,763,062 B2
(45) Date of Patent: Jul. 27, 2010

(54) METHOD AND SYSTEM FOR DELIVERING AND IMPLANTING A GRAFT

(75) Inventors: John Spiridigliozzi, Hyde Park, MA (US); Kristian DiMatteo, Waltham, MA (US); Robert C. Thistle, Bridgewater, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 834 days.

(21) Appl. No.: 10/348,575

(22) Filed: Jan. 21, 2003

(65) Prior Publication Data

US 2004/0143316 A1   Jul. 22, 2004

(51) Int. Cl.
*A61F 2/06* (2006.01)
(52) U.S. Cl. .................... 623/1.11; 623/1.23
(58) Field of Classification Search ....... 623/1.11–1.54, 623/1.1; 606/108, 191, 192, 194, 198, 200
See application file for complete search history.

(56) References Cited

U.S. PATENT DOCUMENTS

| | | | | |
|---|---|---|---|---|
| 4,562,596 | A * | 1/1986 | Kornberg | 623/1.32 |
| 5,151,105 | A | 9/1992 | Kwan-Gett | |
| 5,575,817 | A * | 11/1996 | Martin | 623/1.35 |
| 5,603,698 | A * | 2/1997 | Roberts et al. | 604/104 |
| 5,702,419 | A * | 12/1997 | Berry et al. | 623/1.13 |
| 5,800,540 | A * | 9/1998 | Chin | 128/898 |
| 5,824,055 | A * | 10/1998 | Spiridigliozzi et al. | 623/1.11 |
| 6,019,785 | A | 2/2000 | Strecker | |
| 6,217,585 | B1 | 4/2001 | Whayne et al. | |
| 6,248,116 | B1 * | 6/2001 | Chevillon et al. | 606/139 |
| 6,287,317 | B1 | 9/2001 | Makower et al. | |
| 6,334,864 | B1 | 1/2002 | Amplatz et al. | |
| 6,336,933 | B1 | 1/2002 | Parodi | |

(Continued)

FOREIGN PATENT DOCUMENTS

EP   0 941 715 A2   9/1999

(Continued)

OTHER PUBLICATIONS

Communication pursuant to Article 94(3) EPC, European Patent Office, European Patent Application No. 03 796 938.9-2310, May 16, 2008.

*Primary Examiner*—Ahntuan T Nguyen
*Assistant Examiner*—Kathleen Sonnett
(74) *Attorney, Agent, or Firm*—Vidas, Arrett & Steinkraus P.A.

(57) ABSTRACT

A method and apparatus of treating an abdominal aortic aneurysm in a patient includes the steps of providing a deployable tubular graft of length to extend across the aneurysm. The graft is inserted endovascularly through an artery communicating with the aorta to a site within the aorta whereby an insertion end of the graft is positioned adjacent a non-dilated region of the aorta. The graft is deployed such that the insertion end of the graft is placed against an interior wall of the non-dilated region of the aorta. The graft is held from within the graft against the interior walls of the aorta and while being held, sutures are introduced laparoscopically through a wall of the aorta to the exterior of the graft whereby the graft is sutured to the inner walls of the aorta and the graft.

14 Claims, 8 Drawing Sheets

U.S. PATENT DOCUMENTS

| | | | |
|---|---|---|---|
| 6,364,887 B1 * | 4/2002 | Dworschak et al. | 606/108 |
| 6,364,903 B2 | 4/2002 | Tseng et al. | |
| 2001/0053924 A1 | 12/2001 | Trout, III et al. | |
| 2003/0065385 A1 | 4/2003 | Weadock | |
| 2003/0135269 A1 | 7/2003 | Swanstrom | |

FOREIGN PATENT DOCUMENTS

| | | |
|---|---|---|
| WO | WO 00/07506 | 2/2000 |
| WO | WO 01/60285 | 8/2001 |
| WO | WO 02/41805 | 5/2002 |
| WO | 2004/024034 A2 | 3/2004 |

\* cited by examiner

METHOD AND SYSTEM FOR DELIVERING AND IMPLANTING A GRAFT

FIELD OF THE INVENTION

The present invention relates generally to a method and system for delivering and implanting a graft in a hollow-body organ or vessel, such as the abdominal aorta. More particularly, the present invention relates to a method and system for treating an abdominal aortic aneurysm in a patient.

BACKGROUND OF THE INVENTION

Endoluminal prostheses are typically used to repair, replace, or otherwise correct a diseased or damaged blood vessel. A prosthesis may therefore be used to prevent or treat a wide variety of vascular ailments such as stenosis of the vessel, thrombosis, occlusion, or an aneurysm.

One type of well-known endoluminal prosthesis used in treatment and repair of diseases in various blood vessels is a stent. A stent is a generally longitudinal tubular device which is useful to open and support various lumens in the body. For example, stents may be used in the vascular system, urogenital tract and bile duct, as well as in a variety of other applications in the body. Endovascular stents have become widely used for the treatment of stenosis, strictures, and aneurysms in various blood vessels. These devices are implanted within the vessel to open and/or reinforce collapsing or partially occluded sections of the vessel.

Stents are generally open ended and are radially expandable between a generally unexpanded insertion diameter and an expanded implantation diameter which is greater than the unexpanded insertion diameter. Stents are often flexible in configuration, which allows them to be inserted through and conform to tortuous pathways in the blood vessel. The stent is generally inserted in a radially compressed state and expanded either through a self-expanding mechanism, or through the use of balloon catheters.

A graft is another type of endoluminal prosthesis which is used to repair and replace various body vessels. Whereas a stent provides structural support to hold a damaged vessel open, a graft provides an artificial lumen through which blood may flow. Grafts are typically tubular devices which may be formed of a variety of materials, including textile and non-textile materials. Grafts also generally have an unexpanded insertion diameter and an expanded implantation diameter which is greater than the unexpanded diameter.

It is known to combine a stent and a graft to form a composite endoluminal prosthesis. Such a composite medical device provides additional support for blood flow through weakened sections of a blood vessel. In endovascular applications the use of a stent/graft combination is important because the combination not only effectively allows the passage of blood therethrough, but also ensures the implant will remain open.

It is also known to provide delivery systems for delivering grafts, stents and composite stent/graft prostheses intraluminally. These delivery systems generally include catheters with the prosthesis removably mounted to the distal end of the catheter. Quite often a catheter, introducer sheath, or other similar retaining means, is disposed over the prosthesis to removably support the prosthesis on the catheter. Once the prosthesis is situated in the target site in the lumen, the catheter is removed from the prosthesis.

In treating an abdominal aortic aneurism, traditional open surgery or minimally invasive endovascular procedures may be employed. Traditional open surgery requires a large incision in the abdominal wall, from just below the breast bone to the top of the pubic bone. The muscles are then divided and the intestines and internal organs of the abdomen are pulled aside the aorta in the back of the abdominal cavity, just in front of the spinal column.

The aorta is clamped and the aneurysm is cut open to reveal any plaque and clotted blood inside. Degenerative tissue is then removed. An aortic graft is then sewn to the healthy aortic tissue above and below the weakened area so that, when finished, it functions as a bridge for the blood flow.

After the aortic graft has been sewn in place and all bleeding spots controlled, the aneurysm sack which has been opened along its length is sewn back up usually over the new graft. This prevents the new graft from rubbing against the intestines, which can damage the intestine wall. The entire procedure is fairly traumatic, is relatively high risk, and requires a long recovery period.

The endovascular procedure utilizes the endoluminal prostheses mentioned above to minimally invasively treat an abdominal aortic aneurysm. The endovascular procedure requires two small incisions in the groin. X-ray imaging typically guides the vascular graft, stent, or stent/graft through a blood vessel in the leg and into the aorta.

While minimally-invasive techniques have been an improvement over prior open surgical techniques, there is still need for improvement. A drawback of systems to deliver endoluminal prostheses is the inability to adjust or retrieve the graft or stent/graft once it has been deployed. Generally, deployment of the graft (or stent/graft) marks a point of no return; if the graft is determined to be in an inappropriate position, or the graft size is inadequate, it is not always easy or possible to cancel the procedure or reposition the stent/graft after passing this point.

Another drawback of a known delivery system for delivering stent/grafts is that the large diameter introducer catheters are needed to deliver such systems. A typical previously known stent/graft system may include a central delivery shaft having a diameter of 1.5-1.75 mm, a deployment balloon having a thickness of 0.5-0.75 mm, an anchoring stent with a thickness of 0.3-0.6 mm, a synthetic graft with a thickness of 0.25-0.5 mm, and a delivery sheath having a thickness of 0.5-0.75 mm. A stacking of these thicknesses results in a combined thickness of 4-7 mm, which must be inserted through a vascular system generally having a diameter in the range of 5-7 mm.

This creates apparent problems in the delivery and trauma which may occur with such a prosthesis.

U.S. Pat. No. 5,824,055 to Spiridigliozzi et al. is directed to providing a solution to many of these problems with the delivery systems. The delivery system employed by Spiridigliozzi et al. entails separate delivery of a stent and graft in order to provide a reduced profile and smaller diameter of the system. There are still, however, drawbacks to the system. In particular, once a graft is delivered first before the stent, because there is no anchoring system prior to the stent's introduction, the graft may migrate in the vascular system. This may result in imprecise location and increased trauma to the area. As such, this system requires the use of the stent to lock the graft in place.

Accordingly, it is desirable to provide a system for treating vascular defects and disorders, such as abdominal aortic aneurysms, that minimizes the overall profile of the prosthesis and delivery system and results in a more secure graft/vessel interface.

SUMMARY OF THE INVENTION

In view of the foregoing, it is an object of the present invention to provide a method and system for delivering and implanting a graft in a hollow-body organ or vessel that enables a smaller profile graft and delivery system and results in a more secure graft/vessel interface.

In accordance with one aspect of the invention, a method of implanting a graft in a body vessel comprises the steps of inserting a graft within a body vessel to deliver the graft to a site adjacent a wall of such body vessel. The graft is held against the wall of the body vessel from within the graft and while holding the graft thereagainst, the graft is attached to the wall of the body vessel from outside the graft.

In a particular aspect of the invention, a method is provided for treating an abdominal aortic aneurysm in a patient, wherein the aneurysm has a non-dilated region at opposite ends thereof. The method comprises the steps of providing a deployable tubular graft of length to extend across the aneurysm, the graft having an insertion end. The graft is inserted endovascularly through an artery communicating with the aorta to a site within the aorta such that the graft extends across the aneurysm and the insertion end of the graft is positioned adjacent a non-dilated region of the aorta. The graft is deployed such that the insertion end of the graft is placed against an interior wall of the non-dilated region of the aorta. The graft is held against the interior wall of the aorta and sutures are introduced laparoscopically through a wall of the aorta to the exterior of the graft so that the graft is sutured to the inner wall of the aorta at the insertion end of the graft.

In another aspect of the invention, a system for delivering and implanting a graft in a body vessel comprises a tubular graft and a graft delivery apparatus. The graft delivery apparatus supports the graft interiorly thereof, the apparatus being of size and configuration for endoluminal insertion to a site within the body vessel. The apparatus comprises radially expandable tensioners for deploying the graft within the body vessel and holding the graft in position against the wall of the body vessel. A suture apparatus is provided for laparoscopic introduction to such site of sutures for attaching the graft from outside the graft to the wall of the body vessel.

DETAILED DESCRIPTION OF THE PREFERRED EMBODIMENTS

The present invention provides apparatus and methods for the treatment of aneurysms occurring in hollow-body organs or vessels. As used herein, such hollow-body organs or vessels are collectively referred to as body vessels.

Figure 1:
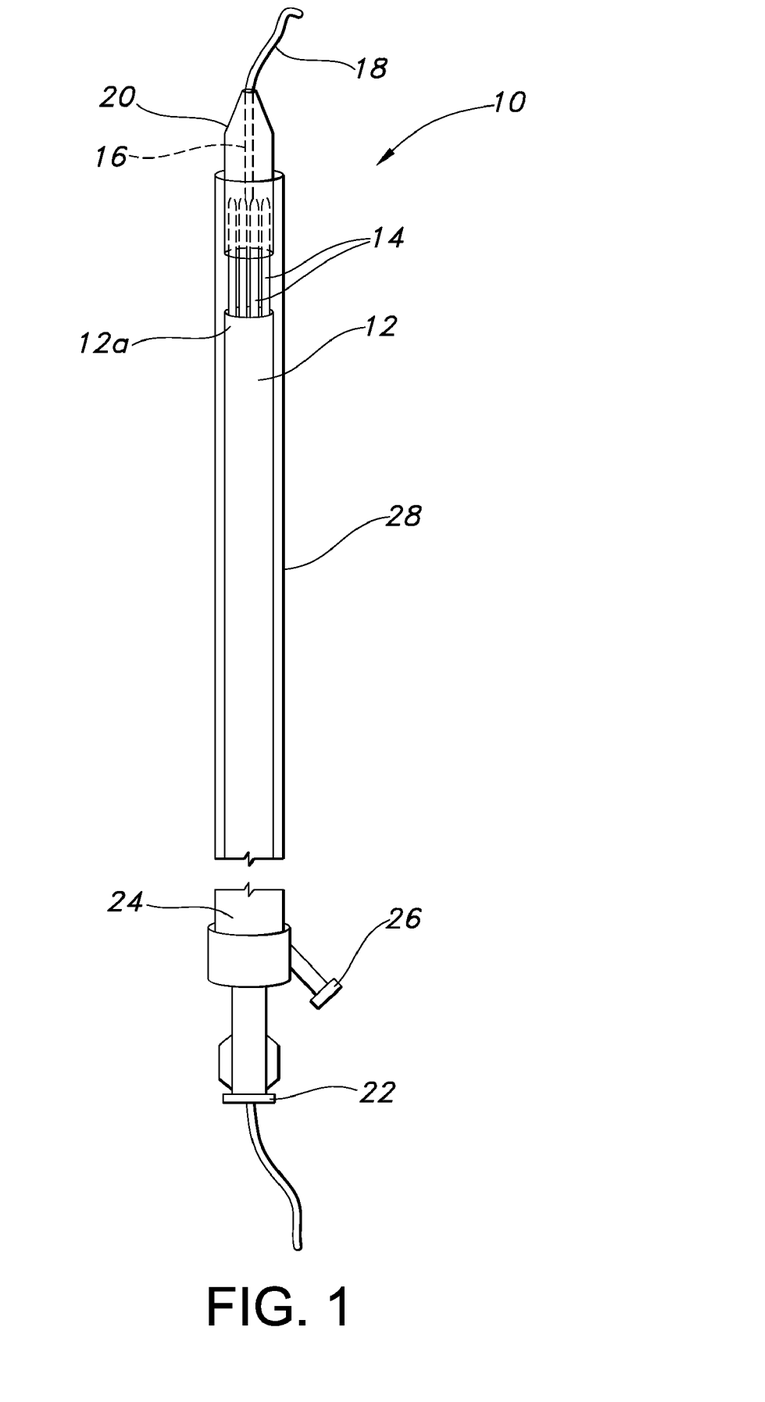
FIG. 1 is a perspective view of a graft delivery system in accordance with one form of the invention with the graft delivery system and graft illustrated in predeployment condition.
Figure 2:
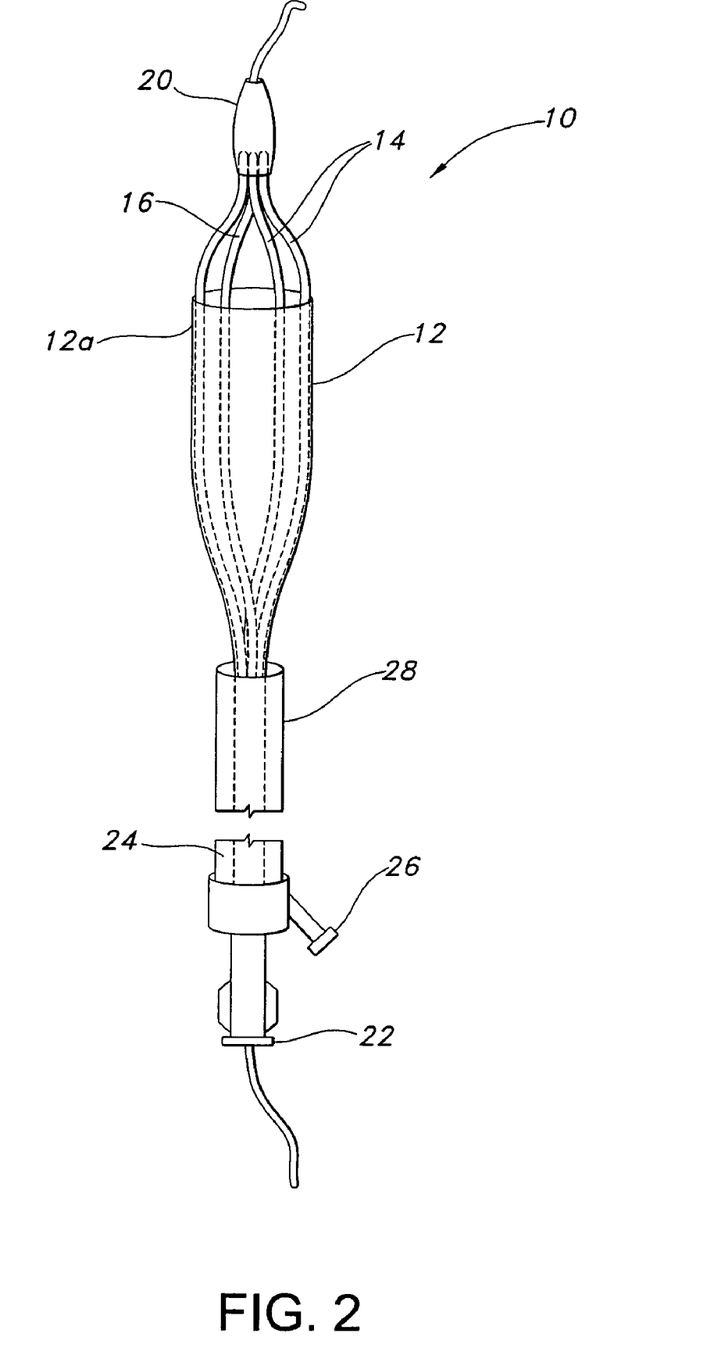
FIG. 2 is a view of the graft delivery system of FIG. 1 illustrating the graft delivery system and graft during deployment.

Referring to FIGS. 1 and 2, a graft delivery system 10 constructed in accordance with the principles of the present invention is described. Graft delivery system 10 is designed to releasably and adjustably grasp a synthetic tubular graft 12. The graft 12 is preferably formed from a polyester fabric, such as polyethylene terepthalate, or other biocompatible material, such as polytetrafluoroethylene (PTFE) or expanded PTFE. In addition, graft 12 may be a biological graft formed of human or animal tissue, rather than synthetic or polymer materials. Such biological grafts may be human homografts, porcine xenografts, allografts or autografts.

Graft delivery system 10 comprises a plurality of radially outwardly expandable graft tensioners 14 that are spaced circumferentially around an inner support tube 16 having an opening through which a guidewire 18 may extend for positioning the graft delivery system 10, as will be described. A nose cone 20 is disposed on the distal end of the support tube to facilitate insertion, of the graft delivery system 10. As used herein with respect to the graft delivery system 10, the term proximal refers to the portion of the graft delivery system that extends outside a patient's body and is manipulated by the clinician, while the term distal refers to the end of the graft delivery system within a patient's body and is furthermost from the proximal end. The distal ends of the graft tensioners 14 are suitably affixed internally of the nose cone 20, while the proximal ends of the graft tensioners 14 are suitably affixed to a movable handle 22 for subsequent removal of the cone 20 and tensioners 14, as will be described.

Adjacent the proximal end, the graft delivery system 10 includes an introducer sleeve 24. A flush port 26 communicating with the interior of the graft delivery system 10 may also be provided for irrigation purposes. Supported internally of the introducer sleeve 24 for slidable longitudinal movement therewith is an outer retractable sheath 28. The distal end of sheath 28 is releasably attached to the nose cone 20 by friction. The tubular graft 12 is disposed interiorly of outer sheath 28 and circumferentially around the graft tensioners 14, with an insertion end 12a of the graft being adjacent the nose cone 20.

In FIG. 1, the graft delivery system 10 is shown as loaded in a predeployment condition. In this condition, the graft tensioners 14 are contracted radially to a reduced delivery diameter by the outer retractable sheath 28 over the graft 12. The radial yield strength of the outer sheath 28 is selected, as is known in the art, to be greater than the outward force produced by the radially expandable tensioners 14, so that the outer sheath 28 biases the tensioners 14 inwardly against the spring force created by tensionsers 14 so that the tensioners 14 are disposed longitudinally adjacent one another and support tube 16. In this condition, the graft 12 is folded within the outer sheath 28 and is held by the sheath 28 against the inherent outward bias of the fingers 14.

Figure 3:
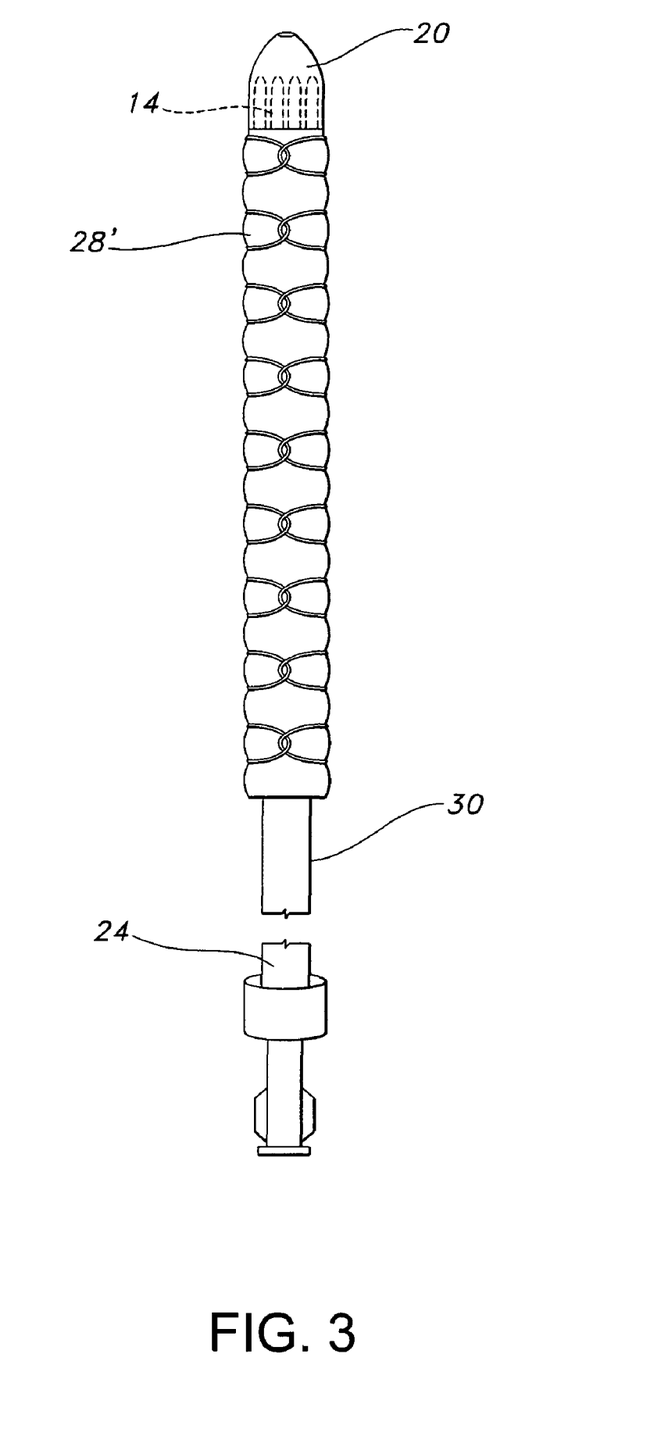
FIG. 3 is a view illustrating an alternative graft delivery system for holding the graft in place prior to insertion and deployment.

As seen in FIG. 2, when the outer sheath 28 is retracted, the graft tensioners 14 move radially outwardly to open the graft 12 substantially to its deployed diameter. While a retractable sleeve 28 has been described herein as retaining the expandable graft tensioners 14 in the reduced diameter predeployment condition, it should be appreciated that other suitable restraining arrangements may be used in the graft delivery system. For example, as shown in FIG. 3, an outer sheath 28' may be used to restrain the expandable graft tensioners 14 in the predeployment condition. Sheath 28' may be constructed in a known crocheted configuration, with an appropriate pull cord 30, whereby upon pulling cord 30, the crocheted construction separates thereby allowing the tensioners to expand to deploy the graft 12 contained within sheath 28' to its deployment diameter. Such a crocheted construction is shown, for example, in U.S. Pat. No. 6,019,785, issued to Ernst Peter Strecker on Feb. 1, 2000, the disclosure of which is incorporated herein by reference. In addition, other suitable graft delivery systems may be used to deploy the graft 12 in the method described herein, such as for example, the delivery system shown and described in U.S. Pat. No. 5,824,055, the disclosure of which is incorporated herein by reference. It should also be understood that while the expandable graft tensioners 14 are shown herein as being relatively straight, alternative tensioners may be used such as a tensioner arranged as a spiral to form a coil or braid.

Figure 4A:
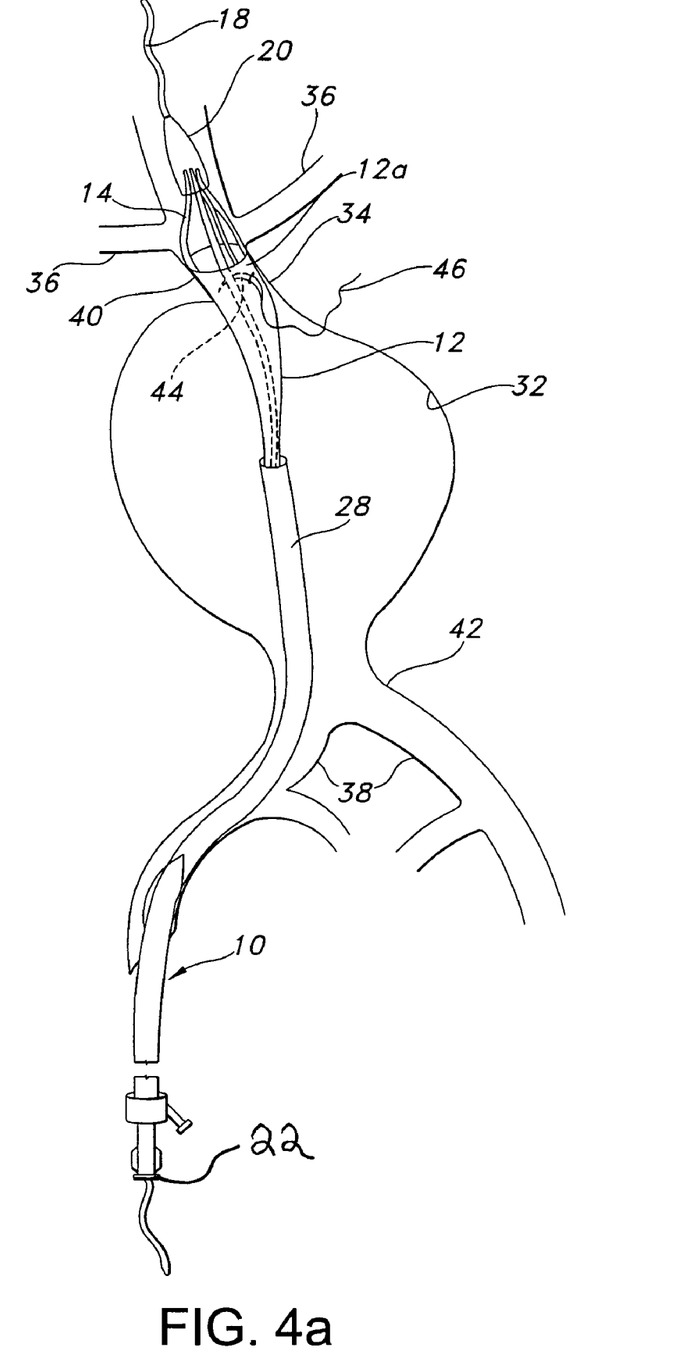
FIGS. 4A, 4B, and 4C are, respectively, perspective views showing deployment of the graft in an abdominal aortic aneurysm and the suturing of the graft to the aorta; the graft as sutured with the partial withdrawal of the graft delivery system; and, the appearance of the graft as permanently implanted in the aorta.
Figure 4B:
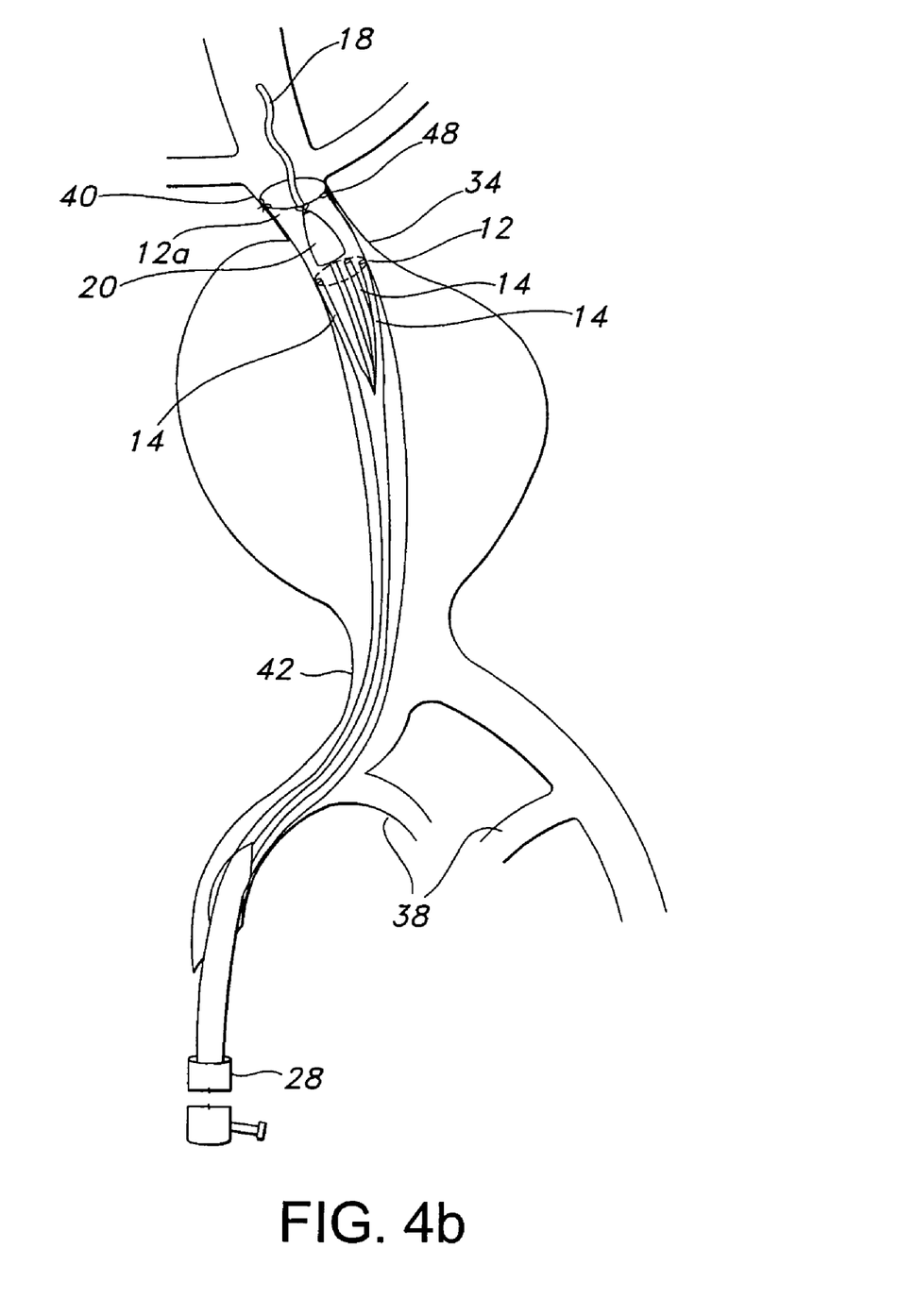
Figure 4C:
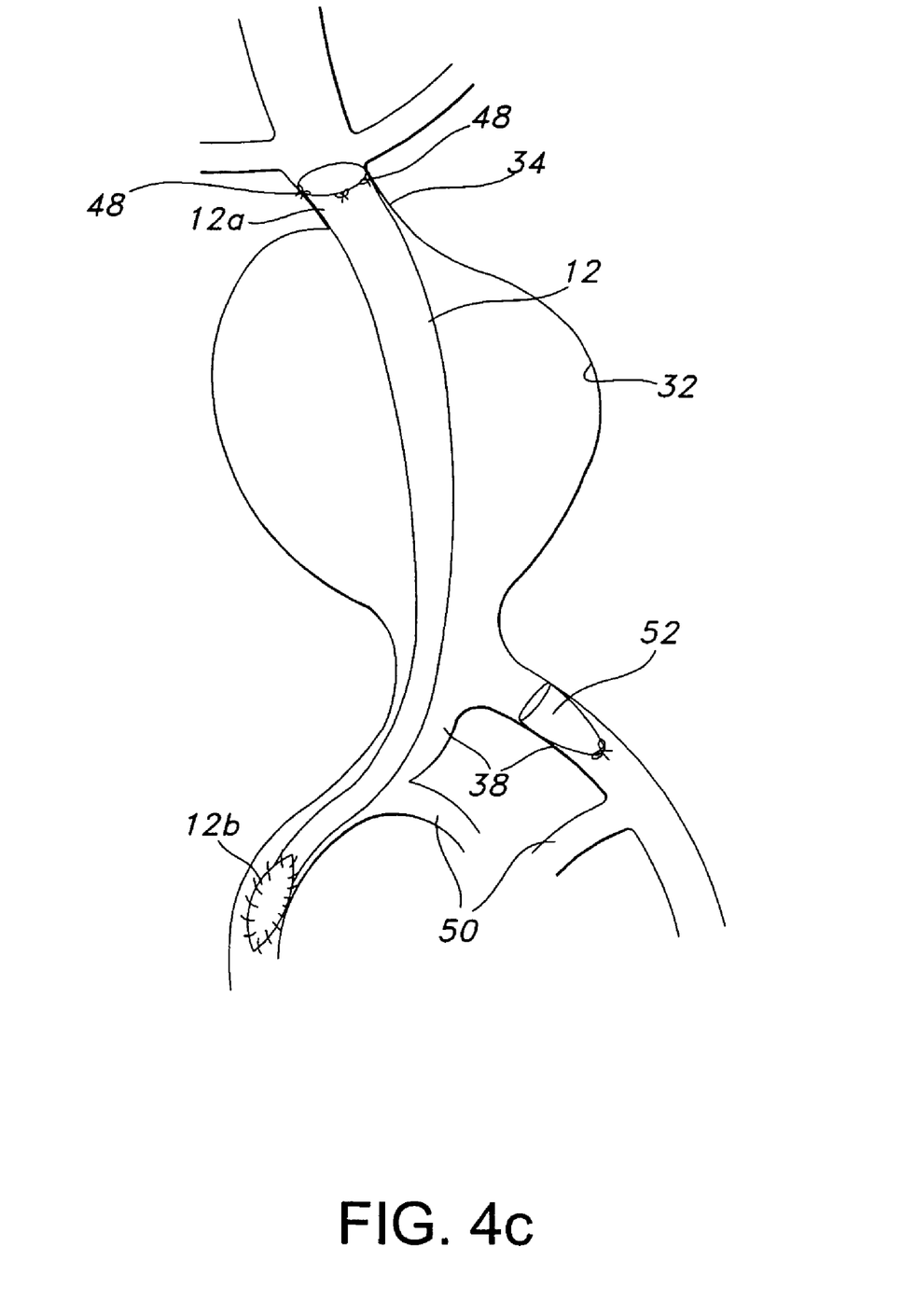

Referring now to FIGS. 4A-4C, a method of implanting a single lumen graft 12 within an abdominal aorta aneurysm 32 using the graft delivery system 10 of the present invention is described.

As depicted in FIG. 4A, the graft delivery system 10 is inserted into the aneurysm 32 over the guidewire 18 until the graft 12 is disposed across aneurysm 32 in the aorta 34 to a position located between the renal arteries 36 and the iliac arteries 38. The aneurysm 32 includes a non-dilated region 40 above the aneurysm 32 (referred to as the "proximal neck") and distal region 42 just above the bifurcation of the iliac arteries 38 (referred to as the "distal cuff"). As used herein with respect to the aneurysm 32, the term proximal means relatively closer to the heart, while the term distal means relatively farther from the heart. The graft delivery system 10 with the introducer sleeve 24 is threaded through a femoral artery along the guidewire 18 until the graft 12 is positioned across aneurysm 32 and the insertion end 12a of the graft 12 is located adjacent the non-dilated proximal neck 40 of the aneurysm 32. The nose cone 20, disposed on the distal end of the graft delivery system 10, facilitates vascular insertion. The position of the graft 12 within aneurysm 32 may be determined using standard fluoroscopic techniques with a suitable high contrast agent or a radiopaque marker on graft 12. Suitable materials may be selected so that the graft 12 may be preferably placed under MRI guidance.

In FIG. 4A, the graft 12 is shown fully deployed from the outer sheath 28, which has been retracted proximally within the graft delivery system 10. Upon retraction of the sheath 28, graft tensioners 14 expand radially outwardly, thereby unfurling graft 12 approximately to its deployed diameter. In particular, graft tensioners 14 urge the insertion end 12a of the graft 12 into engagement with the walls of the non-dilated proximal neck 40 of the aorta 34. The support tube 16 may then moved proximally or distally by movement of handle 22 to maneuver the graft 12 to a desired location across aneurysm 32, for example, under fluoroscopic MRI guidance, so as to adjust the position of the graft within the aneurysm 32. Should the clinician determine that graft 12 is of inappropriate size, or should the clinician wish to abort the procedure, graft 12 may be completely recovered within the outer sheath 28 by moving the graft delivery system 10 outwardly through the non-dilated distal region 42.

Once graft 12 has been positioned to a desired site within aneurysm 32, suitable sutures are introduced laparoscopically through the abdomen to attach the graft 12 to the aorta 34. As shown in FIG. 4A, using conventional laparoscopic techniques, the exterior of the aorta 34 is exposed adjacent the non-dilated region 40 where the insertion end 12a of the graft 12 is internally deployed using appropriate fluoroscopic guidance. A needle 44 with suture 46 attached thereto is then laparoscopically introduced to the exposed aorta 34 from outside thereof. The needle 44 is inserted through the aorta wall and then through the graft 12 into the interior thereof and around the graft tensioner and back through the graft wall and the wall of the aorta where the suture is fixedly tied. In this manner, a number of individual sutures 48, as shown in FIG. 4B, are placed about the graft 12 so as to attach the insertion end 12a of the graft 12 in its deployed diameter so as to maintain an open condition upon attachment to the walls of the aorta 34. Once suturing is completed, the support tube 16 with tensioners 14 and nose cone 20 may then by use of handle 22 be suitably withdrawn by distal movement out through the femoral artery, as shown in FIG. 4B. While attachment of the graft 12 to the aorta 34 is achieved herein by sutures 48, it should be appreciated that other attachment techniques, such as, for example, surgical staples, may also be used.

In FIG. 4 C, the graft 12 is illustrated as permanently implanted in the aorta 34, with the graft delivery system 10 having been completely removed. After removal of the graft delivery system 10 and upon closure of the incision made in the femoral artery for insertion of the graft delivery system 10, the graft may be cut at a location 12b adjacent the incision in the femoral artery where such end 12b may be suitably sutured to the femoral arteriotomy upon closure of the incision in the femoral artery. Further, so as resist backflow of blood into the aneurysm 32 and to encourage blood flow into the interior iliac arteries 50, a contra lateral-iliac occluder 52 is suitably placed in the contra-iliac artery 38, as shown in FIG. 4C. A bifurcated version of a graft for this application may also be used.

Upon withdrawal of the graft delivery system 10, the graft tensioners 14 will slide out from under the nose cone 20 and through the sutures, slightly loosening suture retention, but still sufficient to maintain the graft in place and fully deployed to its expanded diameter.

In accordance with the present invention, the graft delivery system 10 permits the outer sheath 28 to have a smaller diameter, for example, 1-2 mm than previously used devices. Where a stent 54 is used to enhance graft/vessel apposition, the outer diameter of the outer sheath 58 of the stent delivery system 56 may have a diameter of no greater than 18 French. Accordingly, because the individual components of the graft delivery system and, where used, the stent delivery system are relatively small, the respective systems may be introduced through other than the femoral arteries. For example, the graft delivery system may be introduced into the aorta via the brachial artery, while the stents may be delivered to the respective sutured graft site through either a femoral artery or from above via the brachial/carotid arteries.

The methods and apparatus of the present invention have been particularly described with reference to excluding aneurysms occurring in the abdominal aorta. However, the methods and apparatus of the present invention are equally applicable to gastro-intestinal, respiratory, reproductive organ and urethral applications and elsewhere where it is desirable to "reline" a body vessel, and for repairing arterial venous fistulas. In addition, it should be appreciated that while the method and apparatus have been described herein for treating single lumen body vessels, the invention may also be used in conjunction with treating bifurcated lumens of body vessels. Further, the delivery apparatus and methods herein may be used in any size body vessel when properly scaled, such as in the thoracic aorta, superficial femoral artery, iliac artery, as well as to treat neuro aneurysms.

Figure 5:
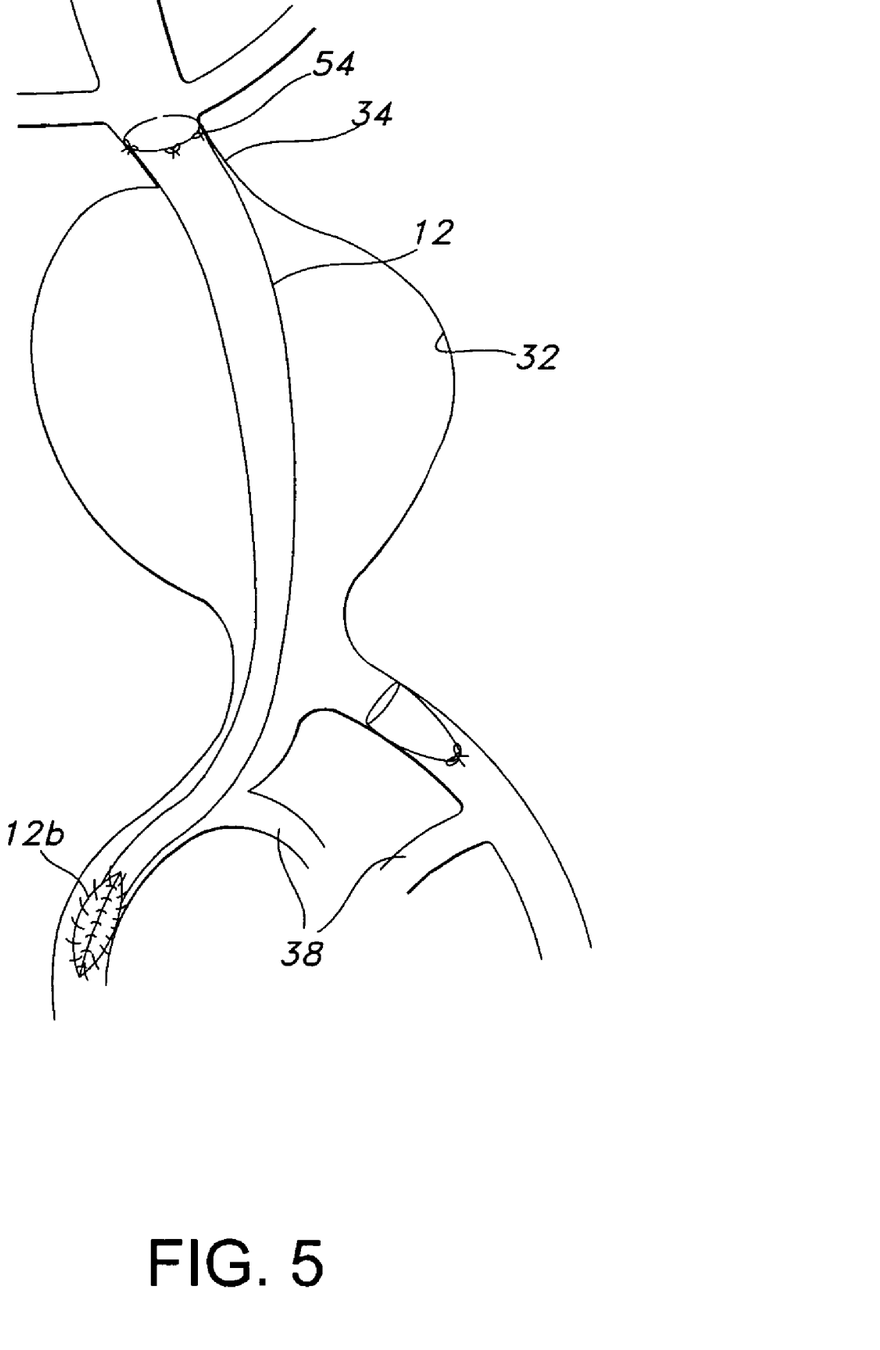
FIG. 5 is a perspective view of an alternative arrangement illustrating the addition of a stent in position within the graft at the sutured site thereof.

While the preferred method of implanting graft 12, has been described herein it should be understood that variations may be made thereto. For example, as shown in FIG. 5, a stent 54 may be placed adjacent the sutured insertion end 12a of the graft 12 to improve graft/vessel apposition. Stents for use in such application may comprise a balloon expandable stent, as described, for example in U.S. Pat. No. 5,443,500 or a self-expanding stent, as described, for example in U.S. Pat. No. 5,147,370, the disclosures of which are incorporated herein by reference.

Figure 6A:
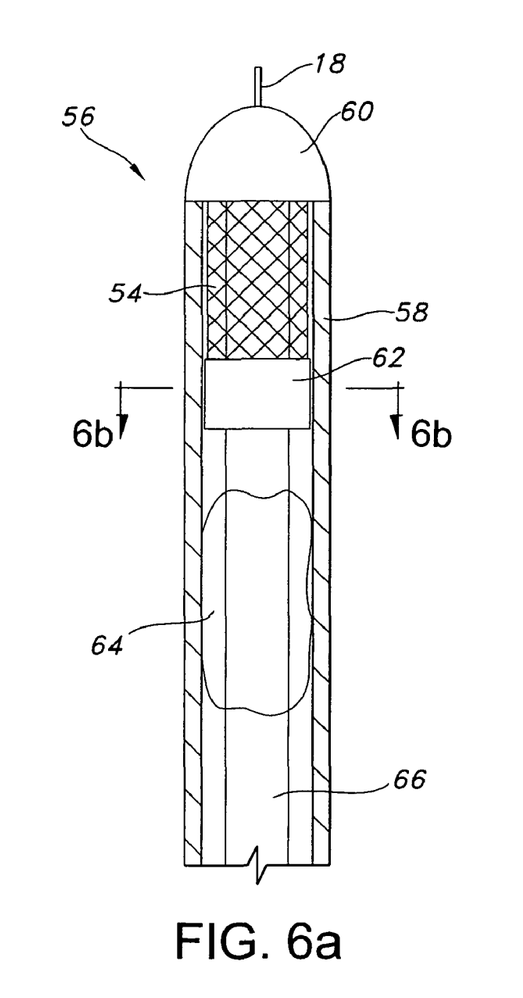
FIGS. 6A and 6B are, respectively, a partial sectional side view and a cross-sectional view along viewing line 6B of FIG. 6A of an illustrative stent delivery system for use in inserting the stent shown in FIG. 5.
Figure 6B:
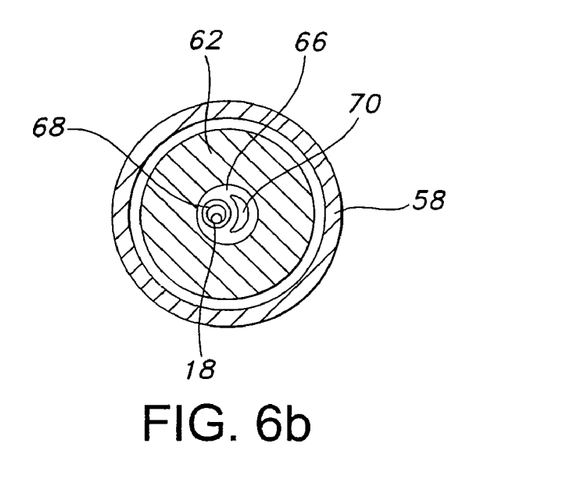

As shown in FIG. 6(a), a stent delivery system 56 includes an outer sheath 58, nose cone 60, core member 66, retaining member 62 and a balloon 64. The stent 54 is disposed within the outer sheath 58 between the nose cone 60 and retaining member 62. As shown in FIG. 6(b), the core member 66 includes a guidewire lumen 68 and an inflation lumen 70 that communicates with the interior of the balloon 64. The guidewire 18, used for the delivery of the graft 12 as described hereinabove, may be inserted through the guidewire lumen 68 to assist in positioning the stent delivery system 56 within the graft 12.

Having described particular arrangements of the present invention herein, it should be appreciated by those skilled in the art that modifications may be made thereto without departing from the contemplated scope thereof. Accordingly, the arrangements described herein are intended to be illustrative rather than limiting, the true scope of the invention being set forth in the claims appended hereto.

What is claimed is:

1. A method of implanting a graft in a body vessel, comprising the steps of:
    inserting a single-insertion graft delivery system within a body vessel to deliver said graft to a site adjacent a wall of such body vessel, said graft having an inside lumen, said single-insertion graft delivery system comprising a plurality of radially expandable longitudinally extending tensioners disposed interiorly within said inside lumen of said graft; a removable outer sheath disposed exteriorly of said graft to maintain said graft in a non-deployed condition until delivered to said site, and a nose cone on the distal end of said delivery system, wherein the distal end of said tensioners are affixed internally of said nose cone, and wherein the distal end of said outer sheath is releasably attached to said nose cone by friction; then
    temporarily holding said graft from within said graft against said wall of said body vessel solely via said tensioners;
    while holding said graft without expansion of the body vessel, attaching said graft to said wall of said body vessel from outside said graft by suturing said graft to said wall laparoscopically,
    wherein said suturing step includes placing at least one suture through the wall of said body vessel, through said graft into the interior thereof, at least a portion of the at least one suture being disposed around at least one of the longitudinally extending tensioners such that the at least one suture overlaps at least one of said tensioners; and
    slidably removing said at least one of said longitudinally extending tensioners from said at least one suture thereby loosening suture retention.

2. The method of claim 1, wherein said body vessel is an artery and wherein the step of inserting the graft is practiced by endovascular delivery.

3. The method of claim 1, wherein said outer sheath is removed when said graft is positioned at said site to thereby allow said tensioners to radially expand to deploy said graft against said wall of said body vessel with said tensioners solely holding said graft in place against said wall.

4. The method of claim 1, further including the step of removing said single-insertion graft delivery system subsequent to the step of suturing.

5. The method of claim 4, further including the step of inserting a stent endovascularly to the desired site of said graft proximate the location of said suturing.

6. The method of claim 1, wherein said method is achieved without occluding said body vessel.

7. The method of claim 1, wherein said tensioners are arranged as a spiral.

8. A method of treating an abdominal aortic aneurysm in a patient, the aneurysm having a non-dilated region at opposite ends thereof, said method comprising the steps of:
    providing a deployable tubular graft of length to extend across said aneurysm, said graft having an insertion end and an inside lumen;
    providing a single-insertion graft delivery system for insertion of said tubular graft, said delivery system having a nose cone at the end of insertion;
    inserting said a single-insertion graft delivery system endovascularly through an artery communicating with said aorta to a site within said aorta such that said graft extends across said aneurysm and said insertion end of said graft is positioned adjacent a non-dilated region of said aorta, said single-insertion graft delivery system comprising a plurality of radially expandable longitudinally extending tensioners disposed interiorly within said inside lumen of said graft and affixed internally of said nose cone, and a removable outer sheath disposed exteriorly of said graft to maintain said graft in a non-deployed condition until delivered to said site, wherein the distal end of said outer sheath is releasably attached to said nose cone by friction;
    deploying said graft by removing said outer sheath and allowing said tensioners to radially expand such that said insertion end of said graft is placed against an interior wall of said non-dilated region of said aorta; then
    temporarily holding said graft against said interior wall of said aorta solely via said tensioners without expanding said aorta;
    laparoscopically introducing an attachment member through a wall of said aorta to the exterior of said graft and attaching said graft to the inner wall of said aorta at the insertion end of said graft,
    attaching said graft by placing at least one suture through the wall of said non-dilated region, through said graft into the interior thereof and around at least one of said longitudinally extending tensioners such that said at least one suture overlaps at least one of said tensioners; and
    slidably removing said at least one of said longitudinally extending tensioners from said at least one suture thereby loosening suture retention.

9. The method of claim 8, wherein deploying said graft includes the step of allowing said expanded tensioners to solely hold said insertion end of said graft against said interior wall of said aorta.

10. The method of claim 8, further including the step of removing said single-insertion graft delivery stem subsequent to the step of attaching the graft to the aorta.

11. The method of claim 10, further including the step of inserting a stent endovascularly to a site proximate the said attached insertion end of said graft.

12. The method of claim 8, wherein said graft is cut to define a second end of said graft, said second end being sutured to said artery through which said graft is inserted at a location adjacent an entry opening in said artery.

13. The method of claim 8, wherein said method is achieved without occluding said body vessel.

14. The method of claim 8, wherein said tensioners are arranged as a spiral.

* * * * *

UNITED STATES PATENT AND TRADEMARK OFFICE
CERTIFICATE OF CORRECTION

| | | |
|---|---|---|
| PATENT NO. | : 7,763,062 B2 | |
| APPLICATION NO. | : 10/348575 | |
| DATED | : July 27, 2010 | |
| INVENTOR(S) | : John Spiridigliozzi, Kristian DiMatteo and Robert C. Thistle | |

It is certified that error appears in the above-identified patent and that said Letters Patent is hereby corrected as shown below:

The title page showing the illustrative figure should be deleted to be replaced with the attached title page.

The drawing sheet, consisting of Fig. 2, should be deleted to be replaced with the drawing sheet, consisting of Fig. 2, as shown on the attached page.

Signed and Sealed this
Fourth Day of January, 2011

David J. Kappos
*Director of the United States Patent and Trademark Office*

(12) United States Patent
Spiridigliozzi et al.

(10) Patent No.: US 7,763,062 B2
(45) Date of Patent: Jul. 27, 2010

(54) METHOD AND SYSTEM FOR DELIVERING AND IMPLANTING A GRAFT

(75) Inventors: John Spiridigliozzi, Hyde Park, MA (US); Kristian DiMatteo, Waltham, MA (US); Robert C. Thistle, Bridgewater, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 834 days.

(21) Appl. No.: 10/348,575

(22) Filed: Jan. 21, 2003

(65) Prior Publication Data

US 2004/0143316 A1 Jul. 22, 2004

(51) Int. Cl.
*A61F 2/06* (2006.01)

(52) U.S. Cl. ............................ 623/1.11; 623/1.23

(58) Field of Classification Search ....... 623/1.11–1.54, 623/1.1; 606/108, 191, 192, 194, 198, 200
See application file for complete search history.

(56) References Cited

U.S. PATENT DOCUMENTS

| | | | |
|---|---|---|---|
| 4,562,596 A * | 1/1986 | Kornberg | 623/1.32 |
| 5,151,105 A | 9/1992 | Kwan-Gett | |
| 5,575,817 A * | 11/1996 | Martin | 623/1.35 |
| 5,603,698 A * | 2/1997 | Roberts et al. | 604/104 |
| 5,702,419 A * | 12/1997 | Berry et al. | 623/1.13 |
| 5,800,540 A * | 9/1998 | Chin | 128/898 |
| 5,824,055 A * | 10/1998 | Spiridigliozzi et al. | 623/1.11 |
| 6,019,785 A | 2/2000 | Strecker | |
| 6,217,585 B1 | 4/2001 | Whayne et al. | |
| 6,248,116 B1 * | 6/2001 | Chevillon et al. | 606/139 |
| 6,287,317 B1 | 9/2001 | Makower et al. | |
| 6,334,864 B1 | 1/2002 | Amplatz et al. | |
| 6,336,933 B1 | 1/2002 | Parodi | |

(Continued)

FOREIGN PATENT DOCUMENTS

EP 0 941 715 A2 9/1999

(Continued)

OTHER PUBLICATIONS

Communication pursuant to Article 94(3) EPC, European Patent Office, European Patent Application No. 03 796 938.9-2310, May 16, 2008.

*Primary Examiner*—Ahntuan T Nguyen
*Assistant Examiner*—Kathleen Sonnett
(74) *Attorney, Agent, or Firm*—Vidas, Arrett & Steinkraus P.A.

(57) ABSTRACT

A method and apparatus of treating an abdominal aortic aneurysm in a patient includes the steps of providing a deployable tubular graft of length to extend across the aneurysm. The graft is inserted endovascularly through an artery communicating with the aorta to a site within the aorta whereby an insertion end of the graft is positioned adjacent a non-dilated region of the aorta. The graft is deployed such that the insertion end of the graft is placed against an interior wall of the non-dilated region of the aorta. The graft is held from within the graft against the interior walls of the aorta and while being held, sutures are introduced laparoscopically through a wall of the aorta to the exterior of the graft whereby the graft is sutured to the inner walls of the aorta and the graft.

14 Claims, 8 Drawing Sheets

FIG. 2